United States Patent [19]
Malone et al.

[11] Patent Number: 6,124,280
[45] Date of Patent: Sep. 26, 2000

[54] SUBSTITUTED PHENOLS AS NOVEL CALCIUM CHANNEL BLOCKERS

[75] Inventors: Thomas C. Malone, Canton; Robert M. Schelkun, Ypsilanti; Po-Wai Yuen, Ann Arbor, all of Mich.

[73] Assignee: Warner-Lambert Company, Morris Plains, N.J.

[21] Appl. No.: 08/983,633

[22] PCT Filed: Jul. 16, 1996

[86] PCT No.: PCT/US96/08064

§ 371 Date: Jan. 23, 1998

§ 102(e) Date: Jan. 23, 1998

[87] PCT Pub. No.: WO97/05125

PCT Pub. Date: Feb. 13, 1997

Related U.S. Application Data

[60] Provisional application No. 60/001,662, Jul. 27, 1995.

[51] Int. Cl.$^7$ ..................................................... A61K 31/55
[52] U.S. Cl. .................... 514/212.01; 540/596; 564/165; 564/306; 544/56; 544/106; 514/12; 514/217.12
[58] Field of Search ............................ 540/596; 514/212, 514/212.01; 564/164, 165, 306; 544/56, 106

[56] References Cited

PUBLICATIONS

CA:77:101011, abs of Zh Obsch Khim 42(4), 940–4 by Kuliev, 1972.
CA:89;129609, abs of Izv Akad Nauk SSSR Ser Khim, (7), pp1621–4 by Ivanov, 1978.
Journal of Chemical society vol. 68, pp. 1894–1901, by Burckhalter, 1946.
Bowersox, "Neuronal Voltage–Sensitive Calcium Channels", *DN&P*, 1994, 7(5):261–268.

*Primary Examiner*—Jean F Vollano
*Attorney, Agent, or Firm*—Elizabeth M. Anderson

[57] ABSTRACT

The present invention relates to novel substituted phenols and derivatives thereof useful in the treatment of neurological disorders. Methods of preparing the compounds, intermediates useful in the preparation and pharmaceutical compositions containing the compounds are also includes.

9 Claims, No Drawings

SUBSTITUTED PHENOLS AS NOVEL CALCIUM CHANNEL BLOCKERS

This application is the national phase of PCT/US96/08064, filed Jul. 16, 1996, now WO 97/05126, which claims priority to provisional application No. 60/001,662 filed Jul. 27, 1995.

The present invention relates to novel substituted bis-(4-hydroxyphenyl)methanes and derivatives thereof useful as pharmaceutical agents, to methods of their production, compositions which include these compounds and a pharmaceutically acceptable carrier, and to pharmaceutical methods of treatment. The novel compounds of the present invention are useful in the treatment of neurological disorders such as traumatic brain injury, cerebral ischemia, stroke, migraine, acute and chronic pain, epilepsy, Parkinson's disease, Alzheimer's disease, amyotropic lateral sclerosis, multiple sclerosis, and depression. The compounds may also be useful for the treatment of nonneurological disorders such as asthma.

The entry of excessive amounts of calcium ion into neurons following an ischemic episode or other neuronal trauma has been well documented. Uncontrolled high concentrations of calcium in neurons initiates a cascade of biochemical events that disrupt normal cellular processes. Among these events are the activation of proteases and lipases, breakdown of neuronal membranes and the formation of free radicals which may ultimately lead to cell death. In particular, the selective N-type calcium channel blocker, SNX-111, has demonstrated activity in a number of models of ischemia and pain (Bowersox S. S., et al., *Drug News and Perspective*, 1994; 7:261–268 and references cited therein).

Therefore, compounds which block N-type calcium channels may be useful in the treatment of neurological disorders such as traumatic brain injury, stroke, migraine, acute and chronic pain, epilepsy, Parkinson's disease, Alzheimer's disease, amyotrophic lateral sclerosis, multiple sclerosis, and depression.

SUMMARY OF THE INVENTION

A compound of formula

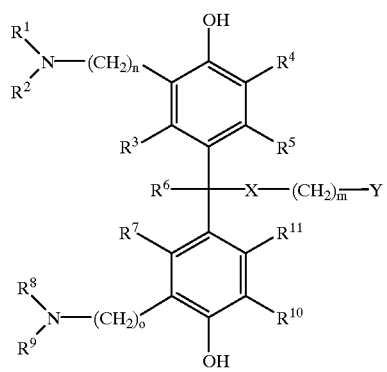

I wherein $R^1$ to $R^{11}$, X, Y, m, n, and o are as defined below are useful in treating various neurological disorders and non-neurological disorders such as asthma.

Preferred compounds of the invention are those of formula

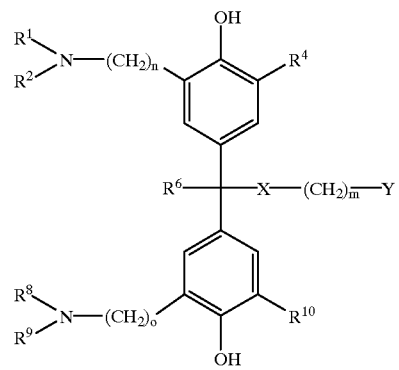

II wherein $R^1$, $R^2$, $R^4$, $R^6$, $R^8$, $R^9$, $R^{10}$, X, Y, m, n, and o are as defined below, and

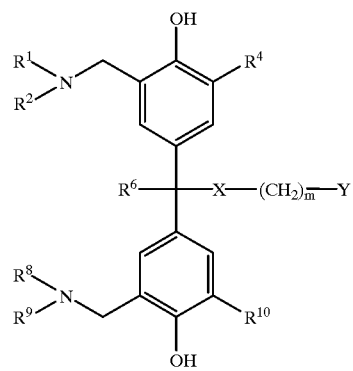

III wherein $R^1$, $R^2$, $R^4$, $R^6$, $R^8$, $R^9$, $R^{10}$, X, Y, and m are as defined below.

Still more preferred compounds are those of Formula III wherein $R^1$, $R^2$, $R^4$, $R^6$, $R^8$, $R^9$, $R^{10}$, Y, and m are as defined below and X is —$(CH_2)_p$— or —$(CH_2)_p$

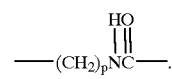

The most preferred compounds are selected from
4,4'-(4-Hydroxy-1-methyl-4,4-diphenylbutylidene) bis[2-[(hexahydro-1H-azepin-1-yl)methyl]phenol],
4,4'-(1Methyl-4,4-diphenylbutylidene)bis[2-[(hexahydro-1H-azepin-1-yl)methyl]phenol],
4,4'-[4-[Bis(phenylmethyl)amino]-1-methyl-butylidene]bis[2-[(hexahydro-1H-azepin-1yl)methyl]phenol],
N-[2,2-Bis-(3-azepan-1-ylmethyl-4-hydroxyphenyl)ethyl] benzamide,
N-[2,2-Bis-(3-azepan-1-ylmethyl-4-hydroxyphenyl)ethyl]-2,2-diphenylacetamide, and
N-[2,2-Bis-(3-azepan-1-ylmethyl-4-hydroxyphenyl)-1-methylethyl]benzamide.

Other aspects of the instant invention are methods of treating neurological disorders such as: traumatic brain injury, cerebral ischemia, acute and chronic pain, epilepsy, Parkinsonism, Alzheimer's disease, amyotrophic lateral sclerosis, multiple sclerosis, and depression. Other disorders such as asthma are also treated.

DETAILED DESCRIPTION

The compounds of the instant invention are those of Formula I

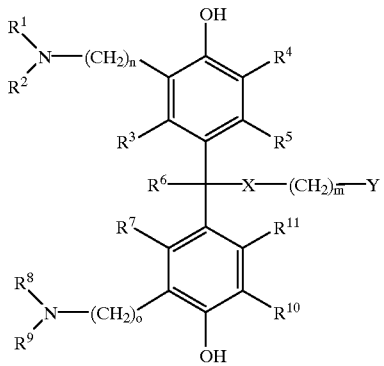

or a pharmaceutically acceptable salt thereof wherein:

$R^1$ and $R^2$ are each independently hydrogen, alkyl, aryl or arylalkyl, or may be taken together with the nitrogen to which they are attached to form a ring of from 4 to 8 carbon atoms, —$CH_2CH_2OCH_2CH_2$—, or —$CH_2CH_2SCH_2CH_2$—;

$R^8$ and $R^9$ are each independently hydrogen, alkyl, aryl or arylalkyl, or may be taken together with the nitrogen to which they are attached to form a ring of from 4 to 8 carbon atoms, —$CH_2CH_2OCH_2CH_2$—, or —$CH_2CH_2SCH_2CH_2$—;

$R^3$, $R^4$, $R^5$, $R^6$, $R^7$, $R^{10}$, and $R^{11}$ are each independently hydrogen, alkyl, or halogen;

X is —$(CH_2)_p$—,
—$(CH_2)_pCONR^{16}$—,
—$(CR^{18}R^{19})_pNR^{16}CO$—, wherein each $R^{18}$ and $R^{19}$ is each independently hydrogen or alkyl of from 1 to 4,
—$(CH_2)_pNR^{16}$—,
—$(CH_2)_pO$—,
—$(CH_2)_pS$—, wherein p is an integer from 0 to 3 and $R^{16}$ is hydrogen or alkyl;

Y is $NR^{12}R^{13}$, $CR^{17}R^{12}R^{13}$, aryl, or heteroaryl wherein $R^{17}$ is hydrogen, hydroxy, or alkyl;

$R^{12}$ and $R^{13}$ are each independently hydrogen, alkyl, aryl, arylalkyl, heteroaryl, or heteroarylalkyl;

n is an integer from 1 to 3;
o is an integer from 1 to 3; and
m is an integer from 0 to 3.

In the compounds of the present invention, the term alkyl, in general and unless specifically limited, means a straight, branched, or cyclic alkyl group of from 1 to 7 carbon atoms including but not limited to methyl, ethyl, propyl, isopropyl, butyl, isobutyl, cyclopentyl, and cyclohexyl.

Aryl refers to a mono- or polycyclic carbocyclic aromatic ring, for example, but not limited to, phenyl and naphthyl. The aryl group may be unsubstituted or substituted by one or more substituents selected from simple alkyl, halogen OH, $OCH_3$, $NO_2$, and $NHCOCH_3$.

Arylalkyl is defined as above in the term alkyl and aryl as is, for example, and not limited to benzyl, 2-phenylethyl, and 3-phenylpropyl.

Heteroaryl is a mono- or polycyclic aromatic ring which contains a heteroatom, for example, but not limited to furanyl, thienyl, and isoquinolinyl.

Heteroarylalkyl is defined as above in the term alkyl and heteroaryl, for example, but not limited to 2-(2-thienyl) ethyl, 2-thienylmethyl, 2-pyridylmethyl, and the like.

Halogen is fluorine, chlorine, bromine, or iodine; fluorine, chlorine, and bromine are preferred.

Carbocyclic ring is a 5- to 7-membered saturated or unsaturated ring and includes, for example, but not limited to cyclopentane, cyclopentene, cyclohexane, cyclohexene, cycloheptane, cycloheptene, indane, and tetralin.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono-, di-, and tricarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.,* 1977; 66:1).

The acid addition salts of said basic compounds are prepared by contacting the free base form with a sufficient amount of the desired acid to produce the salt in the conventional manner. Preferably, a compound of Formula I can be converted to an acidic salt by treating with an aqueous solution of the desired acid, such that the resulting pH is less than four. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma. Sci.,* 1977; 66:1).

The base addition salts of said acidic compounds are prepared by contacting the free acid form with a sufficient amount of the desired base to produce the salt in the conventional manner. Preferably, a compound of Formula I can be converted to a base salt by treating with an aqueous solution of the desired base, such that the resulting pH is greater than nine. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all enantiomeric and epimeric forms as well as the appropriate mixtures thereof.

BIOLOGICAL ACTIVITY

The compounds of the invention exhibit valuable biological properties because of their ability to potently block calcium flux through N-type voltage gated calcium channels. To measure interaction at the N-type calcium channel and calcium flux inhibition, the effects of the calcium channel blockers were measured in the assays described below.

Chick Whole Brain Synaptosomal $^{45}$Calcium Flux Assay

Chicken brain synaptosomes contain voltage sensitive calcium channels which are inhibited by nanomolar concentrations of ω-contoxins and are therefore considered to be primarily N-type (Lundy P. M., Hamilton M. G., Frew R., *Brain Res.*, 1994; 643:204–210). $^{45}$Ca flux into the synaptosomes may be induced by stimulation of the synaptosomal membrane with elevated potassium concentrations. A compound is assessed at various concentrations for its ability to inhibit this potassium stimulated calcium influx.

Methods

One- to five-week old chicks were killed by decapitation and whole brain was removed. The brainstem was discarded, and the remaining brain tissue was placed in ice-cold sucrose buffer (composition: 320 mM sucrose, 5.0 mM TRIS base, 0.1 mM EDTA, pH adjusted to 7.3 with HCl). The total wet weight of pooled brain tissue was determined, and the tissue was homogenized in 10 mL sucrose buffer per gram wet weight. A Potter S-type homogenizer (B. Braun Co.) with a glass tube and teflon pestle was used. Five strokes at 400 rpm were followed by four strokes at 800 rpm. The homogenate was poured into cold centrifuge tubes and centrifuged for 10 minutes at 3000 rpm (1,075 g) in a refrigerated 4° C. RC-5 centrifuge (Sorvall) using an SS-34 rotor. The supernatant was collected and centrifuged at 11,500 rpm (15,800 g) for 10 minutes. The supernatant was discarded, and the pellet was resuspended in 1 mL sucrose buffer. Cold incubation buffer (composition: 1.2 mM $MgCl_2$, 22 mM HEPES, 11 mM glucose, 3 mM KCl, 136 mM choline chloride, pH adjusted to 7.3 with TRIS base) was added slowly to the suspension for a total volume of 30 to 40 mL. This mixture was centrifuged at 7,000 rpm (5,856 g) for 5 minutes. The supernatant was discarded, and the pellet was resuspended in 5 mL of incubation buffer per gram of original wet weight of brain. This synaptosomal suspension was kept on ice until the start of the assay, at which time 35 μL of synaptosome suspension were added to each well of a 96-well filter plate (Millipore) which contained 75 μL incubation buffer with or without drug. Drugs were dissolved in DMSO or $H_2O$, and the concentration of DMSO was less than or equal to 1%.

Synaptosomes were pre-incubated in the presence or absence of drug for 5 minutes at room temperature before the addition of radioactive calcium. Drugs were present throughout the assay. Two μCi/mL stocks of $^{45}CaCl_2$ were prepared in basal buffer (composition: incubation buffer plus 1 mM $CaCl_2$) and in stimulation buffer (composition: 1.2 mM $MgCl_2$, 22 mM HEPES, 11 mM glucose, 37 mM KCl, 102 mM choline chloride, 1 mM $CaCl_2$, pH adjusted to 7.3 with TRIS base). One hundred microliter of radioactive basal or stimulation buffer were pipetted into a pre-incubated plate of synaptosomes using a Quadra 96 pipetter (Tomtec). The final KCl concentration was 3 mM for the basal condition and 20 mM for the stimulated condition; the final $CaCl_2$ concentration was 0.5 mM with 1 μCi/mL of $^{45}CaCl_2$. The plate was filtered under vacuum after a 30-second incubation with radioactivity. The filters were washed twice with 200 μL of wash buffer (composition: 140 mM choline chloride, 3 mM EGTA, 22 mM HEPES, pH adjusted to 7.3 with TRIS base). Plates were allowed to dry completely. Scintillation fluid was added (20 μL/well), and the plates were counted in a Wallace Microbeta plate counter. Basal $^{45}CaCl_2$ flux (3 mM KCl) was subtracted from stimulated $^{45}CaCl_2$ flux (20 mM KCl) in both control and drug-treated conditions, and data were expressed as percent inhibition of the adjusted control response. Values obtained in this way were plotted as a function of drug concentration and $IC_{50}$ values were calculated.

Measurement of N-type Ca2+ Channel Blocking Potencies of Compounds in IMR-32 Cells Using the Fluorescent Ca2+ Indicator Indo-1

IMR-2 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 μM nitrendipine. The remaining component of calcium entry into the IMR-32 cells is due to calcium flux through N-type calcium channels. Intracellular calcium concentrations are measured using the fluorescent calcium indicator Indo-1. The effect of drug concentration on calcium uptake is studied.

Methods

The IMR-32 cell line was obtained from the American Type Culture Collection (Rockville, Md.). Cells were grown in Eagle's Minimum Essential Medium with Earle's salts supplemented with 10% fetal bovine serum, 2 mM L-Gln and antibiotic/antimicotic mixture (Gibco). At approximately 80% confluency, differentiation was induced by the addition of 1 mM dibutyryl cAMP and 2.5 μM bromodeoxyuridine to the medium. After 7 to 13 days of differentiation, cells were detached using 0.5 mM EDTA and loaded with 5 μM Indo-1 acetoxymethyl ester (Molecular Probes, Eugene, Or.) at 30° C. for 45 minutes. Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostatted cuvette holder with stirring capabilities as well as with a computer-controlled pump which allowed for reagent addition during measurement. Instrument control and data collection was done by PTI's OSCAR software running on an IBM compatible computer. Different concentrations of the test compounds (60 μL in dimethyl sulfoxide) were added to 5.94 mL of assay buffer containing approximately 3×$10^6$ loaded cells, and 5 μM Nitrendipine (in 30 μL EtOH) to block L-type $Ca^{2+}$ channels. Samples were incubated for 10 minutes at 30° C. and then aliquoted into three 10×10 mm disposable acrylic cuvettes. Emission signals at 400 and 490 nm were acquired from each cuvette at 30° C. for 50 seconds. At 20 seconds after the start of reading, cells were depolarized by the addition of 160 μL of stimulation solution (1M KCl, 68 mM $CaCl_2$) to the cuvette via the computer-controlled pump. Ratio of dual emission signals (400 nm/490 nm), which is proportional to intracellular $Ca^{2+}$ concentration, was plotted against time, and the difference between maximal response after stimulation and basal value (before stimulation) was determined. Values obtained in this way were plotted as a function of drug concentration. $IC_{50}$ values of test compounds were calculated by fitting a 4-parameter logistic function to the data using the least squares method.

TABLE 1

Inhibition of Calcium Flux in Chicken Synaptosomes and IMR-32 Cells

| Example No. | Inhibition of $^{45}Ca^{+2}$ Influx in Chick Synaptosomes $IC_{50}$ μM | Inhibition of $^{45}Ca^{+2}$ Influx in IMR-32 Cells $IC_{50}$ μM |
| --- | --- | --- |
| 3 | 1.40 | 0.49 |
| 6 | 3.15 | 0.74 |
| 10 | 4.20 | 0.43 |
| 19 | 2.40 | 17.0 |
| 20 | 2.40 | 1.80 |
| 21 | 2.20 | 14.0 |

Table 1 above summarizes the findings of the two assays.

The claimed compounds generally inhibited calcium influx into chicken synaptosomes and IMR-32 cells with $IC_{50}$s of less than 20 μM.

The following nonlimiting examples illustrate the present invention.

EXAMPLE 1

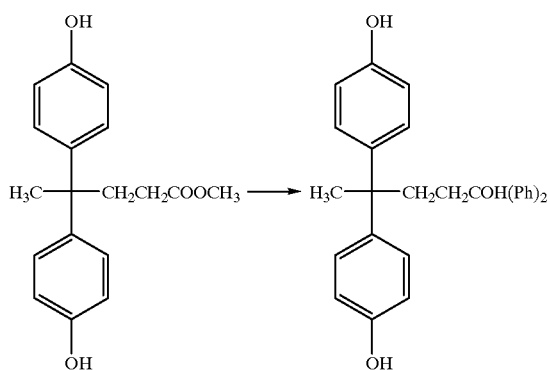

4,4'-(4-Hydroxy-1-methyl-4,4-diphenylbutylidene)-bisphenol

A solution of 4,4-bis(4-hydroxyphenyl)pentanoic acid methyl ester (4.58 g, 15.3 mmol) in 100 mL of anhydrous tetrahydrofuran was cooled to 0° C. and treated dropwise with phenylmagnesium bromide (10 mL of a 3M solution in ether). Additional tetrahydrofuran (50 mL) was added to the reaction mixture followed by phenylmagnesium bromide (10.4 mL of a 3M solution in ether). The reaction was warmed to room temperature and stirred for 3 hours. The reaction was cooled to 0° C. and treated with phenylmagnesium bromide (10.2 mL of a 3M solution in ether). The reaction mixture was warmed to room temperature and stirred for 18 hours. The reaction mixture was cooled to 0° C. and treated with saturated aqueous $NH_4Cl$ solution (100 mL). The organic phase was collected and the aqueous phase was extracted with ethyl acetate (3×100 mL). The combined organic extracts were dried ($MgSO_4$), filtered and concentrated. The residue was purified by chromatography (silica gel, 40% ethyl acetate/hexanes) to give the title compound (6.22 g, 96%) as a white solid.

EXAMPLE 2

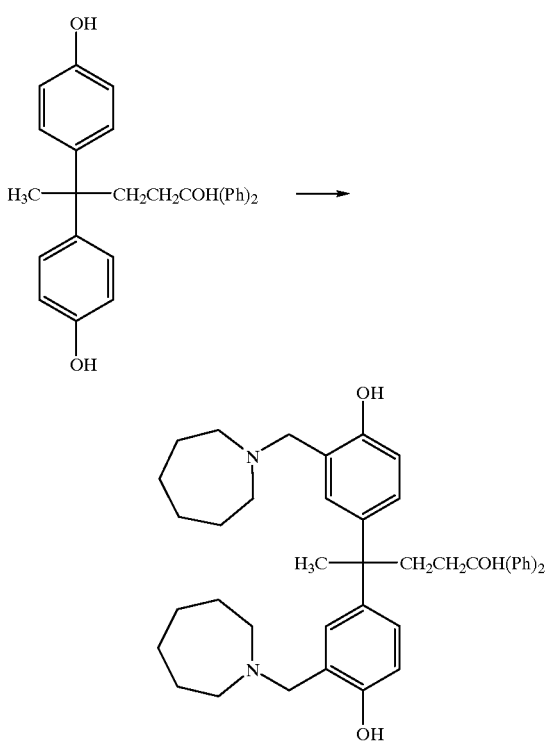

4,4'-(4-Hydroxy-1-methyl-4,4-diphenylbutylidene)bis[2-[(hexahydro-1H-azepin-1-yl)methyl]phenol]

A solution of the compound from Example 1 (1.01 g, 2.36 mmol), hexamethyleneimine (0.53 mL, 4.70 mmol) and 37% aqueous formaldehyde (0.36 mL, 4.80 mmol) in 40 mL of ethanol was heated at 50° C. under nitrogen atmosphere for 72 hours. Additional hexamethyleneimine (0.27 mL, 2.35 mmol) and 37% aqueous formaldehyde (0.18 mL, 2.40 mmol) was added and the reaction mixture heated at 50° C. for 48 hours. The reaction mixture was cooled and concentrated. The residue was dissolved in ethyl acetate (50 mL) and washed with brine (30 mL). The organic phase was dried ($MgSO_4$), filtered, and concentrate. The residue was purified by chromatography (silica gel, 75% ethyl acetate/hexane) to give the title compound.

EXAMPLE 3

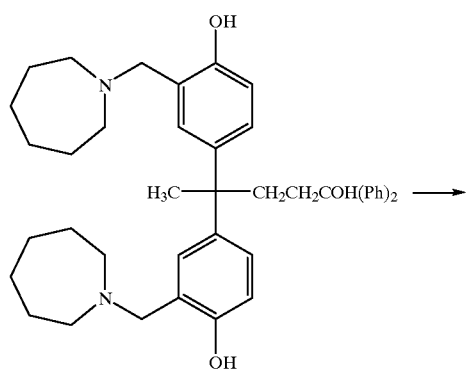

-continued

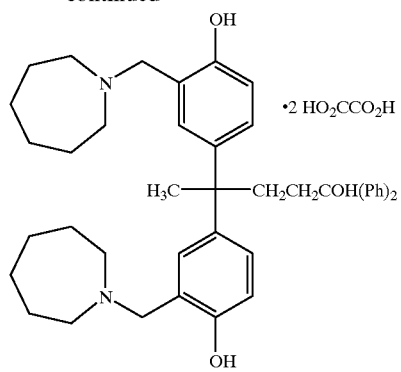

4,4'-(4-Hydroxy-1-methyl-4,4-diphenylbutylidene)bis[2-[(hexahydro-1H-azepin-1-yl)methyl]phenol] oxalic acid salt A solution of the compound from Example 2 (0.27 g, 0.42 mmol) in 6 mL of ether was treated with oxalic acid (0.106 g, 0.84 mmol) in 1 mL of ethanol. The white precipitate which formed was collected and washed with 20 mL of ether. The solid obtained was dried under vacuum ($P_2O_5$) to give the title compound as a white solid, mp=135–150° C.

Analysis calculated for $C_{43}H_{54}N_2O_3 \cdot 2.26\ C_2H_2O_4$:

C, 67.12; H, 6.94; N, 3.30.
Found: C, 67.12; H, 7.16; N, 3.24

EXAMPLE 4

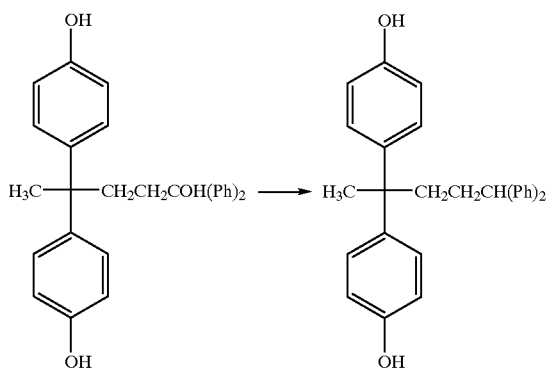

4,4'-(1-Methyl-4,4-diphenylbutylidene)bisphenol

A solution of the product from Example 1 (2.00 g, 4.71 mmol) in 100 mL of methanol was shaken with 20% Pd/C (0.25 g) on a Parr apparatus under a $H_2$ atmosphere (50 psi) for 21 hours. The reaction mixture was filtered and the filtrate concentrated to give the title compound (1.64 g, 85%) as a white foam.

EXAMPLE 5

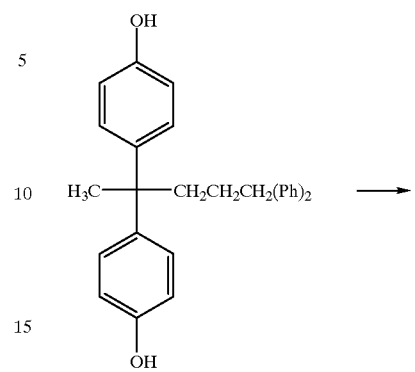

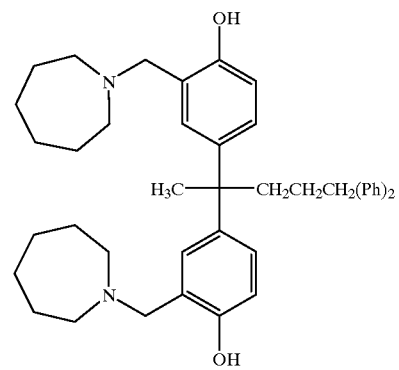

4,4'-(1-Methyl-4,4-diphenylbutylidene)bis[2-[(hexahydro-1H-azepin-1-yl)methyl]phenol]

A solution of the product from Example 4 (0.75 g, 1.84 mmol), hexamethyleneimine (0.42 mL, 3.68 mmol) in 30 mL of ethanol was heated at 50° C. under a $N_2$ atmosphere for 48 hours. The reaction mixture was concentrated and the residue was dissolved in ethyl acetate (75 mL) and washed with brine (30 mL). The combined organic extracts were dried ($MgSO_4$), filtered and concentrated to give the title compound (0.23 g, 20%) as an oil.

EXAMPLE 6

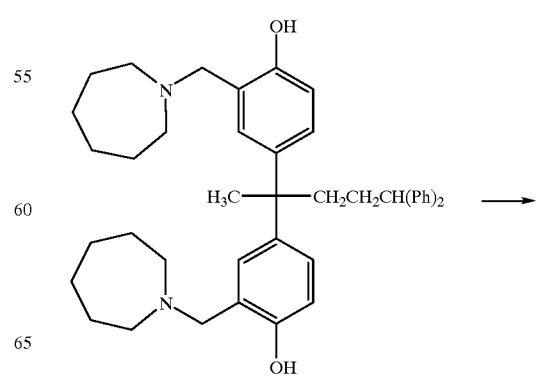

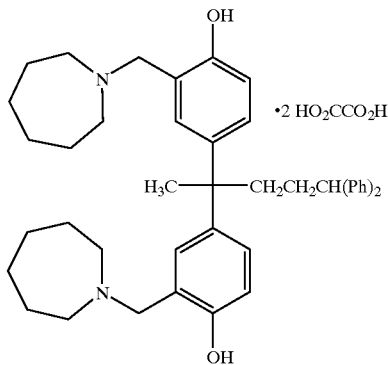

4,4'-(1-Methyl-4,4-diphenylbutylidene)bis[2-[(hexahydro-1H-azepin-1-yl)methyl]phenol] oxalic acid salt The product from Example 5 (0.14 g, 0.22 mmol) was dissolved in 5 mL ether and treated with a solution of oxalic acid (0.564 g, 0.45 mmol) in 1 mL ethanol. The precipitate which formed was collected by filtration the washed with ether. The white solid obtained was dried under vacuum ($P_2O_5$) to give the title compound (0.16 g, 90%), mp=128–164° C.

Analysis calculated for $C_{43}H_{54}N_2O_2.2.0\ C_2H_2O_4$: C, 69.61; H, 7.21; N, 3.45.
Found: C, 70.00; H, 7.21; N, 3.32.

EXAMPLE 7

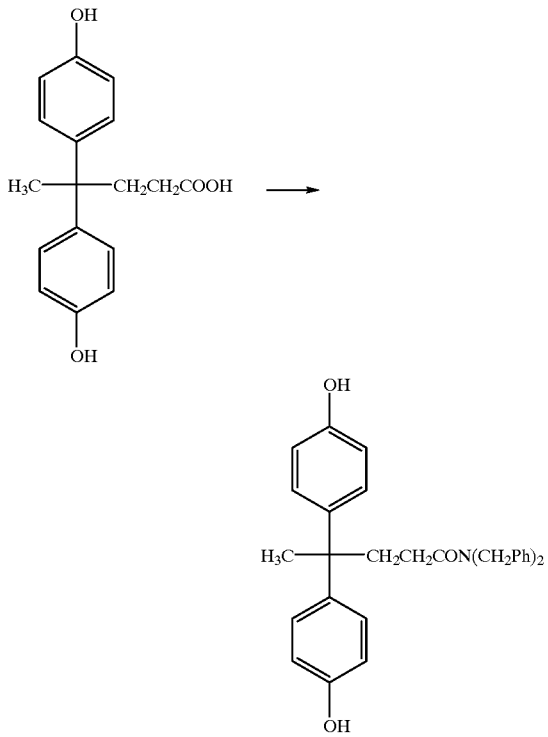

4,4-Bis-(4-hydroxyphenyl)pentanoic acid dibenzylamide

A solution of 4,4-bis-(4-hydroxyphenyl)pentanoic acid (2.00 g, 6.99 mmol) in 40 mL anhydrous tetrahydrofuran was treated with carbonyl diimidazole (3.76 g, 23.2 mmol) and the resulting solution heated at reflux under a $N_2$ atmosphere for 24 hours. Dibenzylamine (5.38 mL, 28 mmol) was then added, and the reaction refluxed again for 48 hours. The reaction mixture was cooled and treated with 10% aqueous HCl solution (50 mL), followed by water (100 mL) and ethyl acetate (200 mL). The organic phase was collected and washed sequentially with water (100 mL) and brine (100 mL). The organic phase was dried ($MgSO_4$), filtered and concentrate. The residue was purified by chromatography (silica gel, 50% ethyl acetate/hexane) to give the title compound (1.30 g, 40%) as a solid, mp=203–207° C.

Analysis calculated for $C_{31}H_{31}NO_3$:

C, 79.97; H, 6.71; N, 3.01.
Found: C, 79.71; H, 6.78; N, 2.87.

EXAMPLE 8

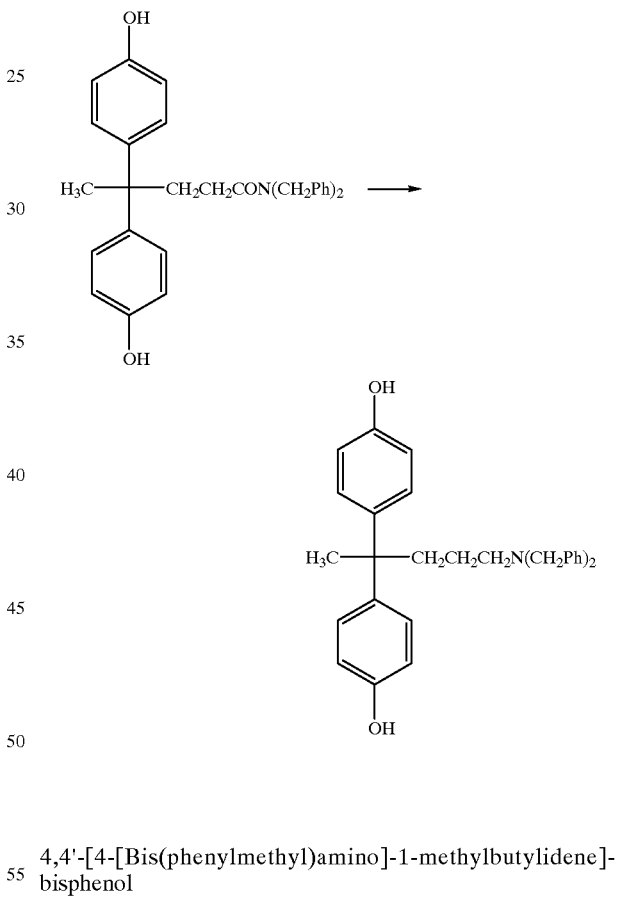

4,4'-[4-[Bis(phenylmethyl)amino]-1-methylbutylidene]-bisphenol

A solution of the product from Example 7 (1.00 g, 2.15 mmol) in 25 mL of anhydrous tetrahydrofuran (THF) was treated dropwise with lithium aluminum hydride solution (4.3 mL of a 1M solution in THF). The resulting solution was heated at reflux for 18 hours. The reaction was cooled and quenched by the addition of saturated $NH_4Cl$ solution and extracted with THF. The combined organic extracts were washed with saturated NaCl solution. The organic phase was dried ($MgSO_4$), filtered, and concentrated to give the title compound (1.03 g, 100%) as a white foam.

EXAMPLE 9

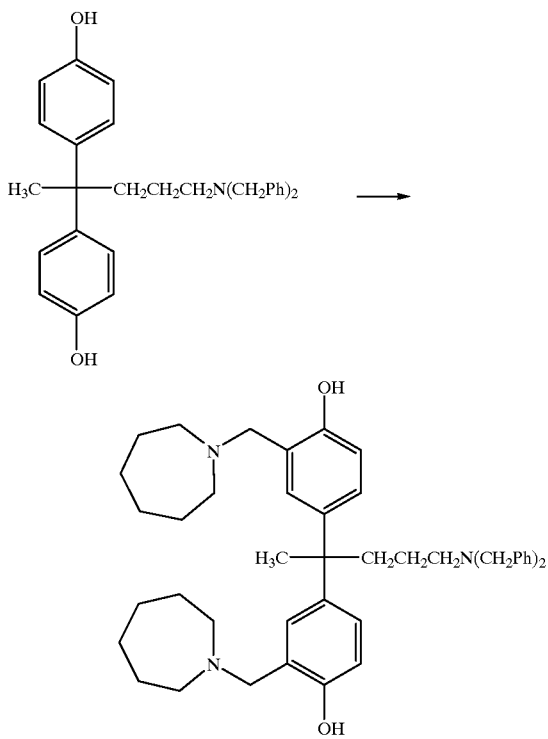

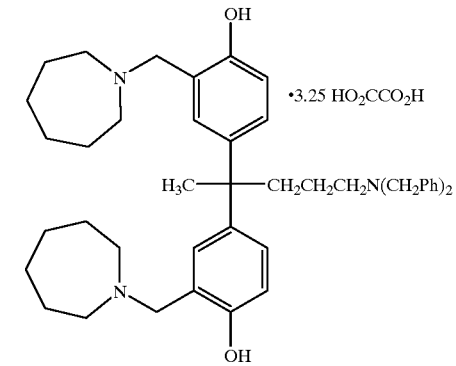

4,4'-[4-[Bis(phenylmethyl)amino]-1-methylbutylidene]-bis[2-[(hexahydro-1H-azepin-1yl)methyl]phenol] oxalic acid salt A solution of the product from Example 9 (0.22 g, 0.33 mmol) in 5 mL Et$_2$O was treated with a solution of oxalic acid (0.13 g, 1.03 mmol) in 1 mL of ethanol. The resulting solution was triturated with 5 mL of Et$_2$O and collected by filtration. The solid collected was washed with Et$_2$O and dried (P$_2$O$_5$) under vacuum to give the title compound (0.28 g, 91%) as a white solid, mp=111–148° C.

Analysis calculated for C$_{45}$H$_{59}$N$_3$O$_2$.3.25 C$_2$H$_2$O$_4$:
C, 64.00; H, 6.83; N, 4.35.
Found: C, 63.98; H, 6.79; N, 4.37.

EXAMPLE 11

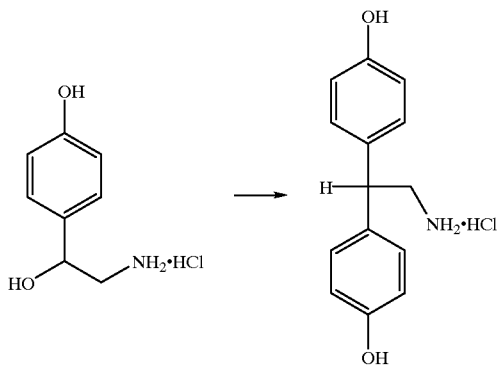

4,4'-(2-Aminoethylidene)bisphenol hydrochloride

According to the method of Kappe and Armstrong, (*J. Org. Chem.*, 1964; 29:826), a solution of octapamine hydrochloride (50 g, 0.264 mol) in 500 mL of aqueous 6N HCl solution was treated with phenol (150 g, 1.59 mol) and the resulting mixture was heated at 100° C. for 48 hours. The reaction mixture was cooled to room temperature and washed with ether. The aqueous phase was concentrated. The residue was dissolved in hot ethanol, decolorized with charcoal, and filtered. The filtrate was treated with ethyl acetate until the solution became slightly cloudy. The solid which formed on cooling was collected by filtration and dried to give the title compound (31.48 g, 0.120 mol) as a white solid, mp=27714 278° C.

Analysis calculated for C$_{14}$H$_{15}$NO$_2$.HCl:
C, 63.28; H, 6.07; N, 5.27; Cl, 13.34.
Found: C, 63.19; H, 6.18; N, 5.28; Cl, 13.32.

A second crop of the title compound (15.9 g, 0.060 mol) was obtained by concentration of the filtrate followed by treatment of the residue with ethanol and ethyl acetate.

4,4'-[4-[Bis(phenylmethyl)amino]-1-methylbutylidene]-bis[2-[(hexahydro-1H-azepin-1yl)methyl]phenol]

A solution of the product from Example 8 (0.93 g, 2.06 mmol), hexamethyleneimine (0.51 mL, 4.53 mmol) and 37% aqueous formaldehyde (0.36 mL, 4.80 mmol) in 20 mL of ethanol was heated at 50° C. for 20 hours under a nitrogen atmosphere. Additional 37% aqueous formaldehyde (0.18 mL, 2.40 mmol) and hexamethyleneimine (0.25 mL, 2.27 mmol) were added and the reaction mixture heated at 50° C. for an additional 48 hours. The reaction mixture was cooled and concentrated. The residue was dissolved in ethyl acetate (50 mL) and washed with water (20 mL) and saturated aqueous NaCl solution. The organic phase was dried (MgSO$_4$), filtered, and concentrated. The residue was purified by chromatography (silica gel, 65% ethyl acetate/hexane) to give the title compound (0.23 g, 17%) as an oil.

EXAMPLE 10

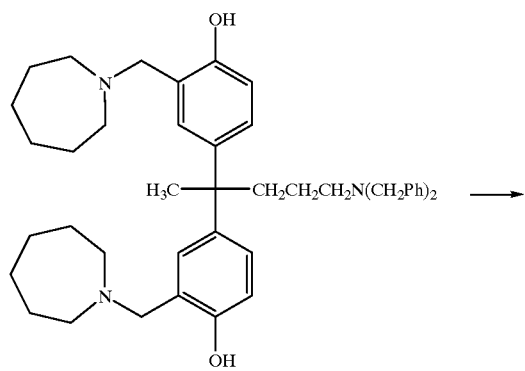

EXAMPLE 12

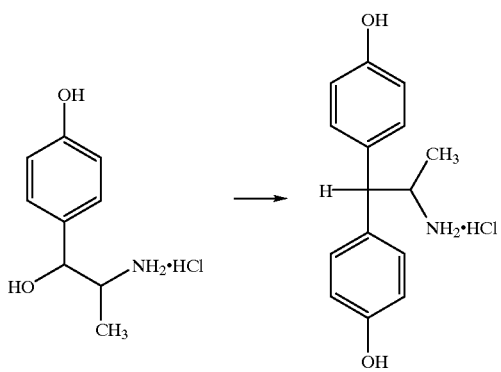

(+/−)-4,4'-(2-Aminopropylidene)bisphenol hydrochloride

According to the method of Kappe and Armstrong (*J. Org. Chem.*, 1964; 29:826), a solution of (±)-α-(1-aminoethyl)-4-hydroxybenzyl alcohol hydrochloride (34.0 g, 0.361 mol) was dissolved in 200 mL of aqueous 6N HCl solution and treated with phenol (10.0 g, 49.1 mmol). The resulting mixture was heated at 100° C. for 6 hours. The reaction mixture was cooled to room temperature and washed with ether (3×50 mL). The aqueous phase was concentrated to give a solid (15.26 g). The solid obtained was suspended in 100 mL of boiling ethanol. The resulting suspension was treated with water (5 mL), and a solution was formed. The resulting solution was treated with ethyl acetate until a persistent cloudiness was obtained. The solid which formed on cooling was collected by suction filtration and dried to give the title compound (7.91 g, 58%) as a white solid, mp=>300° C.

Analysis calculated for $C_{15}H_{17}NO_2 \cdot HCl$:
C, 64.40; H, 6.49; N, 5.01; Cl, 12.67.
C, 64.45; H, 6.43; N, 5.03; Cl, 12.68.

EXAMPLE 13

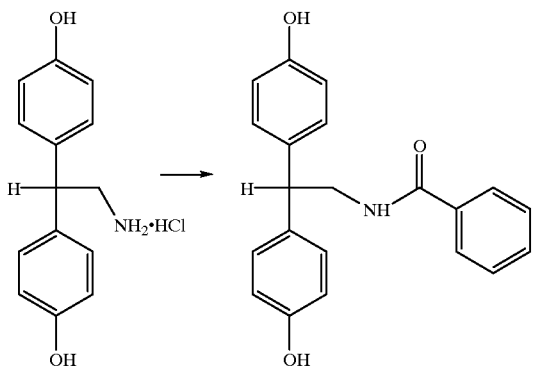

N-[2,2-Bis-(4-hydroxyphenyl)ethyl]benzamide

A solution of the product from Example 11 (5.00 g, 18.8 mmol) was dissolved in tetrahydrofuran (100 mL), dichloromethane (100 mL), saturated aqueous $NaHCO_3$ solution (50 mL), and water (50 mL). The resulting mixture was treated with benzoyl chloride (3.3 mL, 28.2 mmol) and stirred for 4 days. The reaction mixture was extracted with chloroform (3×200 mL). The combined organic extracts were dried ($MgSO_4$), filtered, and concentrated to give the title compound (5.16 g, 82%) as a white solid.

Analysis calculated for $C_{21}H_{19}NO_3$:
C, 75.66; H, 5.74; N, 4.20.
Found: C, 75.32; H, 6.14; N, 3.99.

EXAMPLE 14

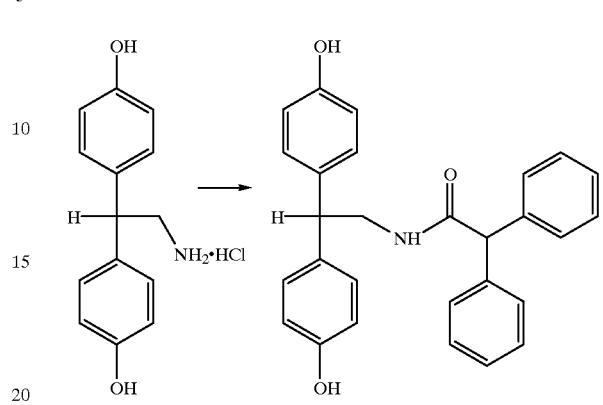

N-[2,2-Bis-(4-hydroxyphenyl)ethyl]-2,2-diphenylacetamide

A solution of the product from Example 11 (5.00 g, 18.8 mmol) was dissolved in tetrahydrofuran (100 mL), dichloromthane (100 mL), saturated aqueous $NaHCO_3$ solution (50 mL), and water (50 mL). The resulting mixture was treated with diphenylacetyl chloride (6.50 g, 28.2 mmol). The reaction mixture was stirred at room temperature until no starting material remained. The reaction mixture was extracted into dichloromethane. The combined organic extracts were dried ($MgSO_4$), filtered, and concentrated. The residue was recrystallized from tetrahydrofuran/diisopropyl ether to give the title compound (5.57 g, 70%) as a white solid.

EXAMPLE 15

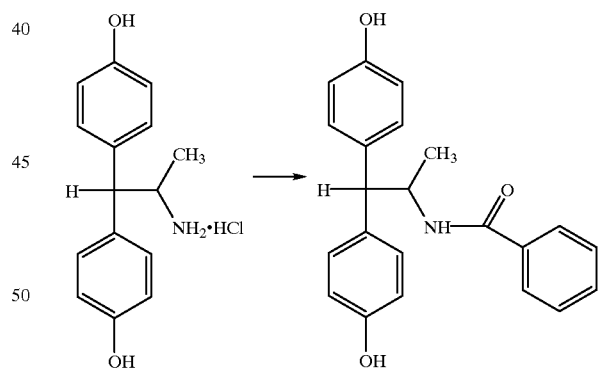

N-[2,2-Bis-(4-hydroxyphenyl)-1-methylethyl]benzamide

The product from Example 12 (5.00 g, 17.0 mmol) was dissolved in chloroform (70 mL), THF (30 mL), and 50 mL saturated aqueous $NaHCO_3$ solution. The reaction mixture was treated with benzoyl chloride (2.5 mL, 21.5 mmol) and the water (25 mL). The reaction mixture was stirred for 5 days. The organic phase was collected, dried ($MgSO_4$), and filtered. The filtrate was concentrated. The residue obtained was dissolved in hot THF and diisopropylether was added until a slight cloudiness developed. The solid which formed on cooling was collected by filtration, washed with additional diisopropylether, and dried under vacuum to give the title compound (4.78 g, 77%) as a white solid.

EXAMPLE 16

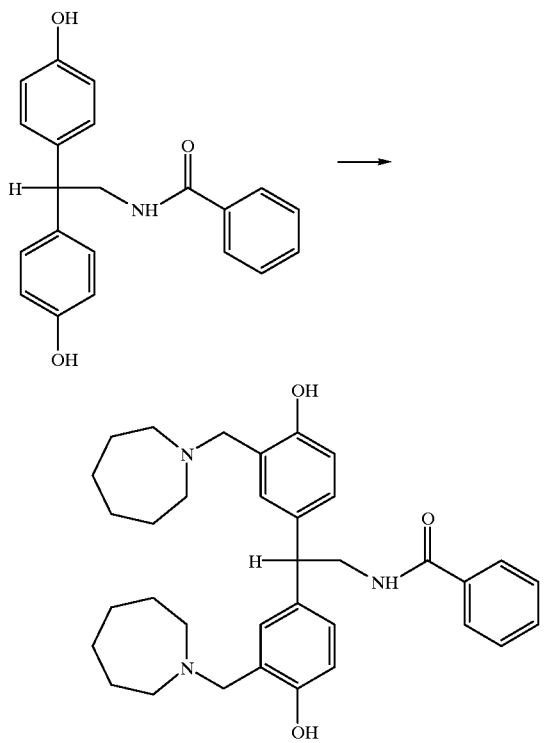

N-[2,2-Bis-(3-azepan-1-ylmethyl-4-hydroxyphenyl)ethyl]-benzamide

A solution of the product from Example 13 (2.00 g, 6.00 mmol) in 40 mL of ethanol was treated with hexamethyleneimine (1.25 g, 12.6 mmol) and 37% aqueous formaldehyde solution (0.90 mL, 12.6 mmol). The resulting solution was heated at reflux for 24 hours. Additional hexamethyleneimine and 37% aqueous formaldehyde solution were added, and the reaction mixture was heated until the starting material was consumed. The reaction mixture was cooled and concentrated. The residue was purified by chromatography (silica gel, 10:1:0.1 EtOAc/EtOH/NH$_4$OH) to give the product as a yellow solid (1.06 g, 32%).

EXAMPLE 17

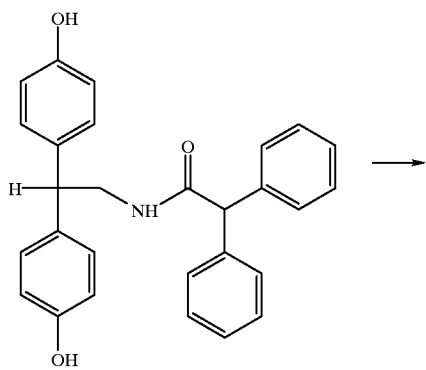

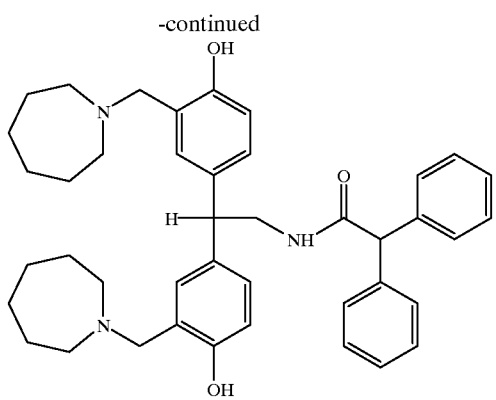

N-[2,2-Bis-(3-azepan-1-ylmethyl-4-hydroxyphenyl)ethyl]-2,2-diphenylacetamide

A solution of the product from Example 14 (2.00 g, 4.72 mmol) in 40 mL of ethanol was treated with hexamethyleneimine (0.98 g, 9.92 mmol) and 37% aqueous formaldehyde solution (0.72 mL, 9.89 mmol). The resulting solution was heated at reflux for 24 hours. Additional hexamethyleneimine and 37% aqueous formaldehyde solution were added and the reaction mixture was heated until the starting material was consumed. The reaction mixture was cooled and concentrated. The residue was purified by chromatography (silica gel, 10:1 EtOAc/EtOH) to give the product as an oil (0.98 g, 32%).

EXAMPLE 18

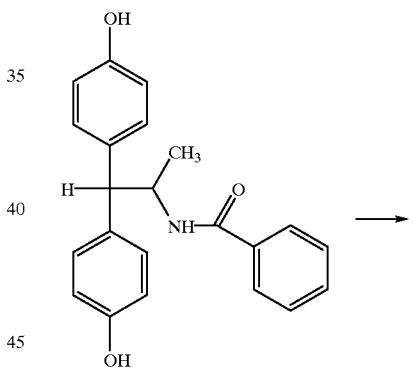

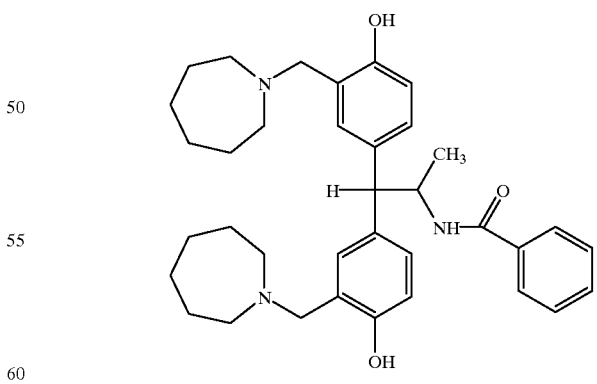

N-[2,2-Bis-(3-azepan-1-ylmethyl-4-hydroxyphenyl)-1-methylethyl]benzamide

A solution of the product from Example 13 (0.50 g, 1.44 mmol) in 20 mL of ethanol was treated with hexamethyleneimine (0.30 g, 3.02 mmol) and 37% aqueous formaldehyde solution (0.21 mL, 2.74 mmol). The resulting solution was heated at reflux for 24 hours. The reaction mixture was cooled and concentrated. The residue was broken up in diisopropyl ether to give the title compound (0.63 g, 81%) as a tan solid.

EXAMPLE 19

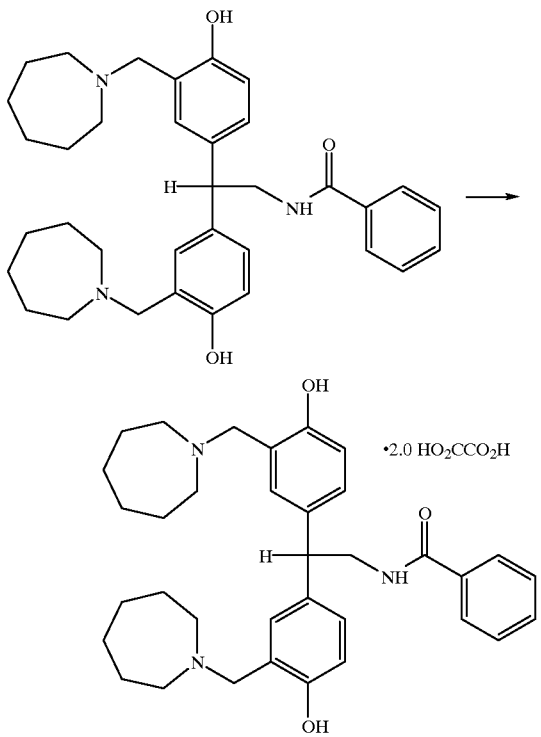

N-[2,2-Bis-(3-azepan-1-ylmethyl-4-hydroxyphenyl)ethyl]-benzamide oxalic acid salt A solution of the product from Example 16 (0.94 g, 1.79 mmol) and oxalic acid (0.26 g, 2.00 mmol) in 5 mL ethanol was triturated with ethyl acetate. The solid which formed was collected by filtration and dried under vacuum at 75° C. to give the title compound (0.875 g, 66%) as a white solid.

Analysis calculated for $C_{35}H_{45}N_3O_3 \cdot 2.00\ C_2H_2O_4$: C, 63.93; H, 6.75; N, 5.75.

Found: C, 63.94; H, 6.82; N, 5.84.

EXAMPLE 20

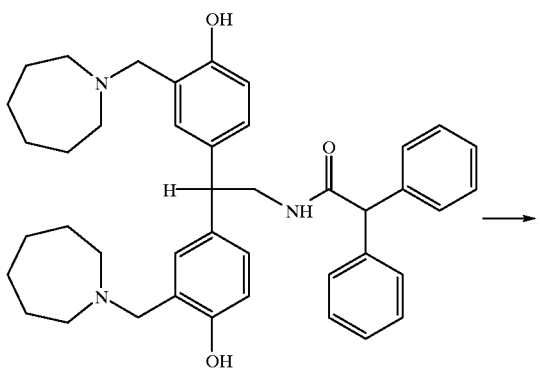

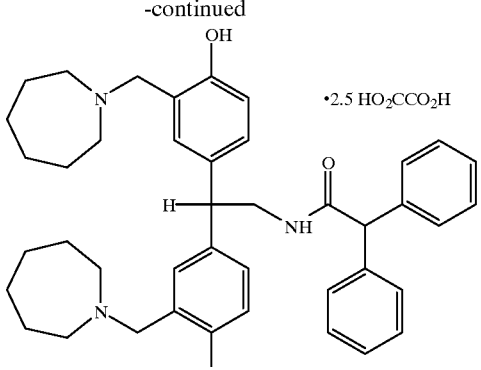

N-[2,2-Bis-(3-azepan-1-ylmethyl-4-hydroxyphenyl)ethyl]-2,2-diphenylacetamide oxalic acid salt A solution of the product from Example 17 (0.89 g, 1.22 mmol) and oxalic acid (0.34 g, 2.66 mmol) in 5 mL ethanol was triturated with isopropanol (20 mL). Ethyl acetate (30 mL) was added and the solid collected by filtration. The solid was dried under vacuum at 75° C. to give the title compound (0.215 g, 20%) as a white solid.

Analysis calculated for $C_{45}H_{451}N_3O_3 \cdot 2.5\ C_2H_2O_4$: C, 61.95; H, 6.59; N, 5.29.

Found: C, 62.06; H, 6.54; N, 5.57.

EXAMPLE 21

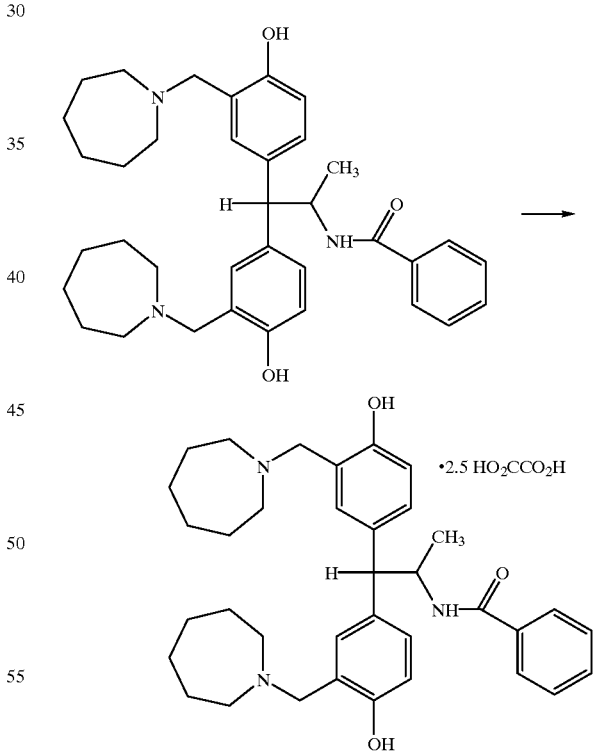

N-[2,2-Bis-(3-azepan-1-ylmethyl-4-hydroxyphenyl)-1-methylethyl]benzamide oxalic acid salt a solution of the product from Example 18 (0.28 g, 0.49 mmol) and oxalic acid (0.13 g, 1.02 mmol) in 5 mL ethanol was triturated with ethyl acetate. The solid which formed was collected by filtration and dried under vacuum at 75° C. to give the title compound (0.097 g, 25%) as a white solid.

Analysis calculated for $C_{36}H_{47}N_3O_3 \cdot 2.5\ C_2H_2O_4$:

C, 61.95; H, 6.59; N, 5.29.
Found: C, 62.06; H, 6.54; N, 5.57.

What is claimed is:

1. A compound of formula

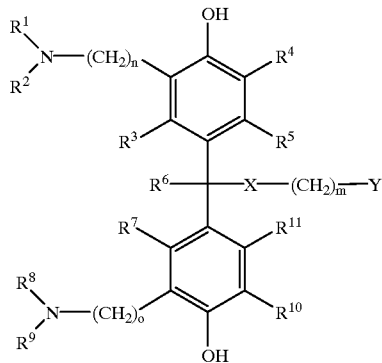

I or a pharmaceutically acceptable salt thereof wherein:

$R^1$ and $R^2$ are each independently hydrogen, alkyl, aryl or arylalkyl, or are taken together with the nitrogen to which they are attached to form a ring of from 4 to 8 carbon atoms;

$R^8$ and $R^9$ are each independently hydrogen, alkyl, aryl or arylalkyl, or are taken together with the nitrogen to which they are attached to form a ring of from 4 to 8 carbon atoms;

$R^3$, $R^4$, $R^5$, $R^6$, $R^7$, $R^{10}$, and $R^{11}$ are each independently hydrogen, alkyl, or halogen;

X is —$(CH_2)_p$—,
—$(CH_2)_p CONR^{16}$—,
—$(CR^{18}R^{19})_p NR^{16}CO$—, wherein each $R^{18}$ and $R^{19}$ is each independently hydrogen or alkyl of from 1 to 4,
—$(CH_2)_p NR^{16}$—,
—$(CH_2)_p O$—,
—$(CH_2)_p S$—, wherein p is an integer of from 0 to 3 and $R^{16}$ is hydrogen or simple alkyl;

Y is $NR^{12}R^{13}$, $CR^{17}R^{12}R^{13}$, or aryl wherein $R^{17}$ is hydrogen, hydroxy or alkyl;

$R^{12}$ and $R^{13}$ are each independently hydrogen, alkyl, substituted aryl wherein the substituents are selected from simple alkyl, OH, $OCH_3$, $NO_2$, and $NHCOCH_3$, arylalkyl, heteroaryl, or heteroarylalkyl;

n is an integer of from 1 to 3;

o is an integer of from 1 to 3; and m is an integer of from 1 to 3; with the proviso that —X—$(CH_2)_m$—Y is not straight or branched alkyl.

2. A compound according to claim 1 wherein $R^3$, $R^5$, $R^{11}$, and $R^7$ are hydrogen.

3. A compound according to claim 1 wherein $R^3$, $R^5$, $R^{11}$, and $R^7$ are hydrogen and n is 1 and o is 1.

4. A compound according to claim 1 wherein $R^3$, $R^5$, $R^{11}$, and $R^7$ are hydrogen, n is 1, o is 1, and X is —$(CH_2)_p$— or

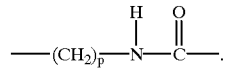

5. A compound selected from 4,4'-(4-Hydroxy-1-methyl-4,4-diphenylbutylidene)-bis [2-[(hexahydro-1H-azepin-1-yl)methyl]phenol], 4,4'-(1-Methyl-4,4-diphenylbutylidene)bis[2-[(hexahydro-1H-azepin-1-yl)methyl]phenol], 4,4'-[4-[Bis(phenylmethyl)amino]-1-methylbutylidene] bis[2-[(hexahydro-1H-azepin-1-yl)-ethyl]phenol], N-[2,2-Bis-(3-azepan-1-ylmthyl-4-hydroxyphenyl)ethyl] benzamide, N-[2,2-Bis-(3-azepan-1-ylmethyl-4-hydroxyphenyl) ethyl]-2,2-diphenylacetamide, and N-[2,2-Bis-(3-azepan-1-ylmethyl-4-hydroxyphenyl)-1-methylethyl]benzamide.

6. A method for treating disorders responsive to the blockade of voltage-gated calcium channels in a mammal in need of said treatment which comprises administering to said mammal a therapeutically effective amount of a compound according to claim 1 in unit dosage form.

7. A pharmaceutical composition comprising a therapeutically effective amount of one or more compounds according to claim 1 together with a pharmaceutically acceptable carrier.

8. A method of treating pain in a mammal suffering therefrom comprising administering a composition according to claim 7 to said mammal.

9. A method of treating cerebral ischemia in a mammal suffering therefrom comprising administering a composition according to claim 7 to said mammal.

* * * * *